US00PP08133P

United States Patent [19]

Holtkamp, Sr.

[11] Patent Number: Plant 8,133

[45] Date of Patent: Feb. 9, 1993

[54] AFRICAN VIOLET PLANT NAMED CATHY

[76] Inventor: Reinhold Holtkamp, Sr., Blumenstrasse 28, D 4242 Rees-Haffen, Fed. Rep. of Germany

[21] Appl. No.: 736,218

[22] Filed: Jul. 26, 1991

[51] Int. Cl.[5] ..... A01H 5/00

[52] U.S. Cl. ..... Plt./69.1

[58] Field of Search ..... Plt./69.1, 69.2

*Primary Examiner*—James R. Feyrer

*Attorney, Agent, or Firm*—Foley & Lardner

[57] ABSTRACT

A new and distinct cultivar of African violet named Cathy characterized by its single violet-shaped, light pink flowers with purplish pink in the center radiating irregularly into the two small petals; strong, upright flower stems that curve slightly toward the center to form a compact bouquet above the leaves; medium green, oval to heart-shaped leaves; profuse flowering, vigorous and compact growth habit, flowering 10–11 weeks after potting, and its long lasting and non-dropping flowers.

1 Drawing Sheet

The present invention comprises a new and distinct cultivar of African violet plant, botanically known as *Saintpaulia ionantha*, and hereinafter referred to by the cultivar name Cathy.

The new cultivar was referred to during the breeding and selection process by the designation 906/58 and is a product of a planned breeding program. The new cultivar was originated from a cross made by me in the controlled breeding program in Haffen, Federal Republic of Germany. The female, or seed parent was a cultivar designated Arizona III. The male, or pollen parent was a cultivar designated 287.

Cathy was discovered and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Cathy has not been observed under all possible enviromental conditions. The phenotype may vary significantly with variations in environment such as temperature, light intensity and day length. The following observations, measurements and values describe the new cultivar as grown in Haffen, West Germany and Nashville, Tenn. under greenhouse conditions which closely approximate those generally used in commercial practice.

The following traits have been repeatedly observed and are determined to be basic characteristics of Cathy, which in combination distinguish this African violet as a new and distinct cultivar:

1) Strong, upright flower stems curving slightly toward the center.

2) Single violet-shaped, very light pink flowers with purplish pink in the center radiating irregularly into the two small petals.

3) Profuse flowering.

4) Each plant carries 8–10 and more upright flower stems each of which carries 6–8 and more flowers.

5) Long lasting, non-dropping flowers.

6) Vigorous and compact grower.

7) Plant saleable 10 to 11 weeks after potting.

8) Seed capsules push slightly through.

9) Medium green, oval to heart-shaped leaves.

10) After maturity the flowers dry off, and remain on the peduncle without becoming infected by botrytis.

The accompanying color photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural sunlight conditions at approximately 12 p.m. in Nashville, Tenn.

Botanical classification: *Saintpaulia ionantha,* Ramat., c.v. Cathy.

Parentage:

*Male parent.*—287.

*Female parent.*—Arizona III.

Propagation: The new cultivar holds its distinguishing characteristics through successive propagations by leaf cuttings.

Plant: From 8 cm to 11 cm tall when grown in pots, and 24–28 cm in diameter when fully grown.

*Leaves.*—General form: Oval to heart-shaped. Diameter: 55–60 mm wide and 65–75 mm long. Texture: Leatherlike. Aspect: Hairy, slightly shiny. Veins: Upperside: visible; underside: well pronounced, light green or purplish pink, shiny. Color (upperside): Yellow-green group 147 A. Color (underside): Greyed-purple group 186 C. Petiole: Strong upright, purplish brown, hairy.

*Flowers.*—Buds: Bell-shaped, light green with purplish pink touch, 5–7 mm just before opening. Sepals: Five (5). Color: Green with purplish brown touch. Calyx: Shape: Funnel-shaped. Aspect: Spear-shaped, hairy. Peduncle: Character: Strong upright, hairy. Color: Purplish brown. Individual flowers: Size: 40–45 mm. Shape: Single violet-shaped, slightly wavy edges. Color (upperside): Purple-violet group 78 ranging from A in the center to D and lighter on the large petals (Some large petals are almost white). Under cooler temperatures and more intensive lighting, the purplish pink tends to intensify. Color (underside): Purple-violet group 78 B to D and lighter (Large petals almost white). Borne: Each flower stem carries 6–8 and more flowers on strong, upright peduncles that are free standing above the leaves, thereby forming a compact bouquet. Flowering habit: Flowers 10–11 weeks after potting.

*Reproductive organs.*—Stamens: Two (2). Anthers: 2 composed of 4 anther cells, seed capsules push slightly through. Filaments: Yellowish green with purplish pink touch, 3–4 mm long. Pollen Color: Yellow group 7 A. Styles: 6–7 mm long, purplish pink, base of ovary light green and hairy.

*Roots.*—Normally developed, white when young, turning slightly brownish when older.

Disease resistance: Up to date, Cathy has shown very good resistance to all major violet diseases.

General observations: Cathy is an attractive cultivar due to its interesting two-tone flowers which are very light pink with purplish pink in the center that radiates irregularly into the two small petals. The petal edges have a purplish pink touch also and are slightly wavy. A tight bouquet of flowers free standing above the leaves develops after 10–11 weeks. Each of the 8–10 and more strong flower stems carries 6–8 and more single violet-shaped flowers. Medium green, oval to heart-shaped leaves surround the flower bouquet. The flowers are long-lasting and non-dropping and the seed capsules push slightly through.

I claim:

1. A new and distinct cultivar of African violet named Cathy, as described and illustrated, and particularly characterized by its single violet-shaped, light pink flowers with purplish pink in the center radiating irregularly into the two small petals; strong, upright flower stems that curve slightly toward the center to form a compact bouquet above the leaves; medium green, oval to heart-shaped leaves; profuse flowering, vigorous and compact growth habit, flowering 10–11 weeks after potting, and its long lasting and non-dropping flowers.

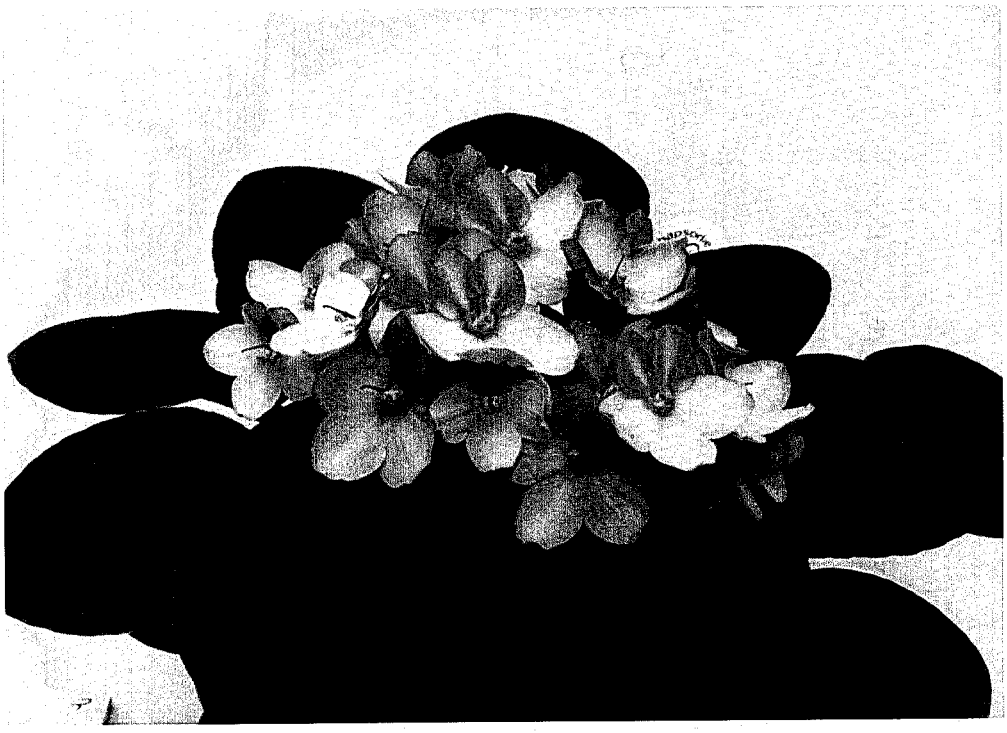

* * * * *